US011530301B2

(12) United States Patent
Mojarradi et al.

(10) Patent No.: US 11,530,301 B2
(45) Date of Patent: Dec. 20, 2022

(54) CARBOHYDRATE CROSSLINKER

(71) Applicant: GALDERMA S.A., Cham (CH)

(72) Inventors: Hotan Mojarradi, Uppsala (SE); Johan Olsson, Bromma (SE); Craig Steven Harris, Biot (FR); Jean-Guy Boiteau, Valbonne (FR); Thibaut Gerfaud, Mouans Sartoux (FR); Loïc Tomas, Biot (FR)

(73) Assignee: Galderma Holding SA, Zug (CH)

( * ) Notice: Subject to any disclaimer, the term of this patent is extended or adjusted under 35 U.S.C. 154(b) by 0 days.

(21) Appl. No.: 16/066,810

(22) PCT Filed: Dec. 28, 2016

(86) PCT No.: PCT/EP2016/082783
§ 371 (c)(1),
(2) Date: Jun. 28, 2018

(87) PCT Pub. No.: WO2017/114867
PCT Pub. Date: Jul. 6, 2017

(65) Prior Publication Data
US 2019/0023812 A1    Jan. 24, 2019

(30) Foreign Application Priority Data

Dec. 29, 2015 (EP) .................................. 15202944
May 31, 2016 (EP) .................................. 16172225
May 31, 2016 (EP) .................................. 16172241
May 31, 2016 (EP) .................................. 16172254

(51) Int. Cl.
| | | |
|---|---|---|
| A61K 8/04 | (2006.01) | |
| A61K 8/73 | (2006.01) | |
| A61P 17/00 | (2006.01) | |
| A61Q 19/00 | (2006.01) | |
| A61K 9/00 | (2006.01) | |
| C08B 37/08 | (2006.01) | |
| C08K 5/09 | (2006.01) | |
| C08K 5/08 | (2006.01) | |
| C07C 209/62 | (2006.01) | |
| C07C 7/08 | (2006.01) | |
| C07C 213/00 | (2006.01) | |
| C08J 3/24 | (2006.01) | |
| C08J 3/075 | (2006.01) | |
| C08L 5/00 | (2006.01) | |
| C08J 7/14 | (2006.01) | |
| C07C 269/06 | (2006.01) | |
| C08B 37/00 | (2006.01) | |
| C08L 5/08 | (2006.01) | |
| C07F 7/08 | (2006.01) | |

(52) U.S. Cl.
CPC .............. *C08J 3/075* (2013.01); *A61K 8/042* (2013.01); *A61K 8/73* (2013.01); *A61K 8/735* (2013.01); *A61K 9/0019* (2013.01); *A61Q 19/00* (2013.01); *C07C 209/62* (2013.01); *C07C 213/00* (2013.01); *C07C 269/06* (2013.01); *C07F 7/083* (2013.01); *C08B 37/0063* (2013.01); *C08B 37/0069* (2013.01); *C08B 37/0072* (2013.01); *C08J 3/24* (2013.01); *C08J 7/14* (2013.01); *C08K 5/09* (2013.01); *C08L 5/00* (2013.01); *C08L 5/08* (2013.01); C07C 2603/18 (2017.05); C08J 2305/00 (2013.01); C08J 2305/08 (2013.01)

(58) Field of Classification Search
CPC ....... C08L 5/00; C08K 5/09; C08J 7/14; C08J 3/24; C08J 3/075; C08B 37/0072; C08B 37/0069; C08B 37/0063; C07F 7/083; C07C 269/06; C07C 213/00; C07C 209/62; A61Q 19/00; A61K 9/0019; A61K 8/73; A61K 8/735; A61K 8/042
See application file for complete search history.

(56) References Cited

U.S. PATENT DOCUMENTS

| | | |
|---|---|---|
| 5,332,812 A | 7/1994 | Nicolson et al. |
| 5,731,298 A | 3/1998 | Reinmuller |
| 6,132,750 A | 10/2000 | Perrier et al. |
| 6,495,314 B1 | 12/2002 | Kent et al. |
| 6,703,444 B2 | 3/2004 | Zhao et al. |
| 6,831,172 B1 | 12/2004 | Barbucci et al. |
| 7,731,758 B2 | 6/2010 | Asius et al. |
| 8,414,657 B2 | 4/2013 | Asius et al. |
| 8,858,999 B2 | 10/2014 | Giammona et al. |
| 8,887,243 B2 | 11/2014 | Thomson et al. |
| 10,105,197 B1 | 10/2018 | Colon |

(Continued)

FOREIGN PATENT DOCUMENTS

| | | |
|---|---|---|
| CN | 1529716 A | 9/2004 |
| CN | 1570128 A | 1/2005 |

(Continued)

OTHER PUBLICATIONS

Kurita (Macromolecules, published 1994, pp. 7544-7549) (Year: 1994).*
Hoffman (Organic Chemistry, An Intermediate Text, Second Edition, p. 187, 2004) (Year: 2004).*
Tokita (Polymer Degradation and Stability, pp. 269-273, Published 1995 (Year: 1995).*
Stern (Biotechnology Advances, pp. 537-557, Published 2007) (Year: 2007).*
International Search Report (PCT/ISA/210) dated Jul. 31, 2017, by the European Patent Office as the International Searching Authority for International Application No. PCT/EP2017/063029.

(Continued)

*Primary Examiner* — Alma Pipic
(74) *Attorney, Agent, or Firm* — Sunit Talapatra; Foley & Lardner LLP

(57) ABSTRACT

The invention relates to a hydrogel product comprising glycosaminoglycan molecules as the swellable polymer, wherein the glycosaminoglycan molecules are covalently crosslinked via crosslinks comprising a spacer group selected from the group consisting of di-, tri-, tetra-, and oligosaccharides.

11 Claims, No Drawings

(56) References Cited

U.S. PATENT DOCUMENTS

| | | |
|---|---|---|
| 2003/0093157 A1 | 5/2003 | Casares et al. |
| 2004/0072793 A1 | 4/2004 | Aeschlimann et al. |
| 2004/0219630 A1 | 11/2004 | Tsubouchi |
| 2006/0166928 A1 | 7/2006 | Moon et al. |
| 2007/0053987 A1 | 3/2007 | Bayer et al. |
| 2007/0065481 A1 | 3/2007 | Chudzik et al. |
| 2007/0066816 A1 | 3/2007 | Tsai et al. |
| 2009/0011045 A1 | 1/2009 | Mertin et al. |
| 2009/0247741 A1 | 10/2009 | Zhao |
| 2010/0136070 A1* | 6/2010 | Dobak |
| 2010/0255068 A1* | 10/2010 | Stroumpoulis |
| 2012/0231046 A1 | 9/2012 | Asius et al. |
| 2013/0085187 A1 | 4/2013 | Kim et al. |
| 2013/0203697 A1 | 8/2013 | Hashimoto et al. |
| 2013/0338352 A1 | 12/2013 | Yasugi et al. |
| 2014/0094568 A1 | 4/2014 | James et al. |
| 2015/0045573 A1 | 2/2015 | Cheng et al. |
| 2016/0106718 A1 | 4/2016 | Gupta |
| 2019/0016830 A1 | 1/2019 | Olsson et al. |
| 2019/0023812 A1 | 1/2019 | Mojarradi et al. |
| 2019/0023855 A1 | 1/2019 | Olsson et al. |

FOREIGN PATENT DOCUMENTS

| | | |
|---|---|---|
| CN | 1694903 A | 11/2005 |
| CN | 102952281 | 3/2013 |
| CN | 103038339 A | 4/2013 |
| CN | 103788222 A | 5/2014 |
| CN | 104194066 A | 12/2014 |
| DE | 44 39 575 A1 | 5/1996 |
| EP | 0 224 987 | 6/1987 |
| EP | 0 903 152 A2 | 3/1999 |
| EP | 1 837 347 A1 | 9/2007 |
| EP | 2 609 924 A1 | 7/2013 |
| EP | 2 682 409 A1 | 1/2014 |
| EP | 2 727 597 A1 | 5/2014 |
| EP | 3 020 733 A1 | 5/2016 |
| JP | S62-265998 A | 11/1987 |
| JP | H11-152234 A | 6/1999 |
| JP | 2014-531433 A | 11/2014 |
| JP | 2015-537078 A | 12/2015 |
| WO | 97/11958 A1 | 4/1997 |
| WO | 00/01733 A1 | 1/2000 |
| WO | 00/46252 A1 | 8/2000 |
| WO | 00/46253 A1 | 8/2000 |
| WO | 02/18450 A1 | 3/2002 |
| WO | 02/30990 A1 | 4/2002 |
| WO | 02/081739 A2 | 10/2002 |
| WO | 02/082078 A2 | 10/2002 |
| WO | WO-2004/011503 A1 | 2/2004 |
| WO | WO-2004/057008 A1 | 7/2004 |
| WO | WO-2007/026362 A2 | 3/2007 |
| WO | WO-2013/086024 A2 | 6/2013 |
| WO | WO-2014/072330 A1 | 5/2014 |
| WO | WO-2015/021092 | 2/2015 |
| WO | WO-2015/034436 | 3/2015 |
| WO | 2015/181365 A1 | 12/2015 |
| WO | 2015/181369 A1 | 12/2015 |
| WO | WO-2017/114861 | 7/2017 |
| WO | WO-2017/114864 | 7/2017 |
| WO | WO-2017/114865 | 7/2017 |
| WO | WO-2017/114867 A1 | 7/2017 |
| WO | WO-2019/002368 A1 | 1/2019 |
| WO | WO-2019/002370 A1 | 1/2019 |

OTHER PUBLICATIONS

Written Opinion (PCT/ISA/237) dated Jul. 31, 2017, by the European Patent Office as the International Searching Authority for International Application No. PCT/EP2017/063029.

International Search Report (PCT/ISA/210) dated Feb. 20, 2017, by the European Patent Office as the International Searching Authority for International Application No. PCT/EP2016/082778.

International Search Report (PCT/ISA/210) dated Feb. 20, 2017, by the European Patent Office as the International Searching Authority for International Application No. PCT/EP2016/082781.

International Search Report (PCT/ISA/210) dated Feb. 22, 2017, by the European Patent Office as the International Searching Authority for International Application No. PCT/EP2016/082783.

International Search Report (PCT/ISA/210) dated Feb. 23, 2017, by the European Patent Office as the International Searching Authority for International Application No. PCT/EP2016/082774.

International Search Report (PCT/ISA/210) dated May 10, 2017, by the European Patent Office as the International Searching Authority for International Application No. PCT/EP2016/082770.

Written Opinion (PCT/ISA/237) dated Feb. 20, 2017, by the European Patent Office as the International Searching Authority for International Application No. PCT/EP2016/082778.

Written Opinion (PCT/ISA/237) dated Feb. 20, 2017, by the European Patent Office as the International Searching Authority for International Application No. PCT/EP2016/082781.

Written Opinion (PCT/ISA/237) dated Feb. 22, 2017, by the European Patent Office as the International Searching Authority for International Application No. PCT/EP2016/082783.

Written Opinion (PCT/ISA/237) dated Feb. 23, 2017, by the European Patent Office as the International Searching Authority for International Application No. PCT/EP2016/082774.

Written Opinion (PCT/ISA/237) dated May 10, 2017, by the European Patent Office as the International Searching Authority for International Application No. PCT/EP2016/082770.

Borke, Tina, et al., "Optimized triazine-mediated amidationfor efficient and controlled functionalization of hyaluronic acid", Carbohydrate Polymers 115, pp. 42-50, 2015.

Canova-Davis, Eleanor, et al., "Chemical heterogeneity as a result of hydroxylamine cleavage of a fusion protein of human insulin-like growth factor I", Biochem. J., vol. 285, pp. 207-213, 1992.

D'Este, Matteo, et al., "A systematic analysis of DMTMM vs EDC/NHS for ligation of amines to Hyaluronan in water", Carbohydrate Polymers 108 , pp. 239-246, 2014.

Schanté, Carole E, et al., "Chemical modification of hyaluronic acid for the synthesis of derivatives for a broad range of biomedical applications", Carbohydrate Polymers 85 , pp. 469-489, 2011.

Tomihata, Kenji, et al., "Crosslinking of hyaluronic acid with water-soluble carbodiimide", Research Center for Biomedical Engineering, pp. 243-251, 1995-1996.

Tsigos, Iason, et al., "Chitin deacetylases: new, versatile tools in biotechnology", TIBTECH, vol. 18, pp. 305-312, Jul. 2000.

Zhu, Jeff X., et al., "Selective cleavage of isoaspartyl peptide bonds by hydroxylamine after methyltransferase priming", Analytical Biochemistry 364, pp. 1-7, 2007.

Crimmins et al. (Current Protocols in Protein Science (2005) 11.4.1-11.4.11) (11 pages).

Maleki et al.; "Characterization of the chemical degradation of hyaluronic acid during chemical gelation in the presence of different cross-linker agents"; Carbohydrate Research, vol. 342, pp. 2776-2792; (2007) (17 pages).

Olson et al. (The Journal of Biological Chemistry, vol. 260, No. 6, Issue of Mar. 25, pp. 3784-3790, 1985) (7 pages).

Sara Rydergren; "Chemical Modifications of Hyaluronan using DMTMM-Activated Amidation"; Uppsala Universitet; Aug. 2013 (English Abstract only) (35 pages).

Gómes-Reyes, et al., "Metal-catalyzed hydroxylaminolysis of unactivated amide and peptide bonds," Org. Biomol. Chem., vol. 1, 2003, pp. 866-872 (7 pages).

Babasola, Oladunni, et al., "Chemically Modified N-Acylated Hyaluronan Fragments Modulate Proinflammatory Cytokine Production by Stimulated Human Macrophages," The Journal of Biological Chemistry, vol. 289, No. 36, pp. 24779-24791, Sep. 5, 2014.

Lauder R.M., "Chondroitin sulphate: A complex molecule with potential impacts on a wide range of biological systems", Complementary Therapies in Medicine, 2009, vol. 17, pp. 56-62 (7 pages).

Paterson et al., "Carbohydrate-Based Crosslinking Agents: Potential Use in Hydrogels", Journal of Polymer Science Part A: Polymer Chemistry, vol. 49, pp. 4312-4315 (4 pages), Published 2011.

(56) References Cited

OTHER PUBLICATIONS

Gupta et al., "Hydrogels for wound healing applications", Biomedical Hydrogels Biochemistry, 2011, pp. 184-227.
Ohshima et al., "Cleavage of unactivated amide bonds by ammonium salt-accelerated hydrazinolysis", ChemComm, 2014, pp. 12623-12625 (4 pages).
Ohshima et al., "Microwave-Assisted Deacylation of Unactivated Amides using Ammonium-Salt-Accelerated Transamidation", Angewandte Communications, 2012, vol. 51, pp. 8564-8567 (4 pages).
Werner et al., "Regulation of Wound Healing by Growth Factors and Cytokines", Physiol Rev, 2003, vol. 83, pp. 835-870.
International Search Report and Written Opinion on PCT Appl. Ser. No. PCT/IB2020/061336 dated Mar. 1, 2021 (9 pages).
International Search Report and Written Opinion on PCT PCT/IB2020/060066 dated Jan. 12, 2021 (14 pages).

\* cited by examiner

CARBOHYDRATE CROSSLINKER

TECHNICAL FIELD OF THE INVENTION

The present invention relates to the field of hydrogels containing crosslinked polysaccharides and the use of such hydrogels in medical and/or cosmetic applications. More specifically, the present invention is concerned with hydrogels made of crosslinked glycosaminoglycans, particularly crosslinked hyaluronic acid, chondroitin or chondroitin sulfate.

BACKGROUND OF THE INVENTION

Water-absorbing gels, or hydrogels, are widely used in the biomedical field. They are generally prepared by chemical crosslinking of polymers to infinite networks. While many polysaccharides absorb water until they are completely dissolved, crosslinked gels of the same polysaccharides can typically absorb a certain amount of water until they are saturated, i.e. they have a finite liquid retention capacity, or swelling degree.

Hyaluronic acid, chondroitin and chondroitin sulfate are well-known biocompatible polymers. They are naturally occurring polysaccharides belonging to the group of glycosaminoglycans (GAGs). All GAGs are negatively charged heteropolysaccharide chains which have a capacity to absorb large amounts of water.

Hyaluronic acid (HA) is one of the most widely used biocompatible polymers for medical and cosmetic use. HA is a naturally occurring polysaccharide belonging to the group of glycosaminoglycans (GAGs). Hyaluronic acid and products derived from hyaluronic acid are widely used in the biomedical and cosmetic fields, for instance during viscosurgery and as a dermal filler.

Chondroitin sulfate (CS) is a highly abundant GAG found in the connective tissues of mammals where it, together with other sulfated GAGs, is bound to proteins as part proteoglycans. It has previously been shown that hydrogels containing CS successfully can be used in biomedical applications due to their resemblance to the natural extra cellular matrix (Lauder, R. M., Complement Ther Med 17: 56-62, 2009). Chondroitin sulfate is also used in the treatment of osteoarthritis, e.g. as a dietary supplement.

Crosslinking of the glycosaminoglycans prolongs the duration of the degradable polymers that make up the network, which is useful in may application. However, the crosslinking can also reduce the native properties of the glycosaminoglycans. Hence, it is typically desired to maintain a low degree of modification by efficient crosslinking to conserve the native properties and effects of the glycosaminoglycan itself.

SUMMARY OF THE INVENTION

It is an object of the present invention to provide a hydrogel having a glycosaminoglycan (GAG) as the swellable polymer.

It is a further object of the present invention to provide a method for crosslinking GAG molecules with reduced effect of the native properties of the GAG molecules.

It is also an object of the present invention to provide a method for preparing hydrogels of GAG molecules by mild and efficient routes.

For these and other objects that will be evident from this disclosure, the present invention provides according to a first aspect a hydrogel product comprising glycosaminoglycan molecules as the swellable polymer, wherein the glycosaminoglycan molecules are covalently crosslinked via crosslinks comprising a spacer group selected from the group consisting of di-, tri-, tetra-, and oligosaccharides.

With reference to the inventive processes of preparing hydrogel products described herein, the term "crosslinker" refers to a molecule having two or more functional groups, particularly nucleofile functional groups attached to a non-reactive spacer group, particularly a di-, tri-, tetra-, or oligosaccharide.

Each of the two or more functional groups is capable of reacting with carboxylic acid groups on the GAG molecules to form stable covalent bonds. Preferably, the crosslinker consists of the two or more functional groups and the spacer.

With reference to the inventive hydrogel products described herein, the term "crosslink" refers to the portion, or residue, of the crosslinker by which the GAG molecules are covalently linked after crosslinking. The crosslink typically consists of i) the spacer group and ii) the binding groups formed upon reaction of the functional groups of the crosslinker with the carboxylic acid groups on the GAG. The spacer group may for example be comprised of a hyaluronic acid tetrasaccharide, hyaluronic acid hexasaccharide, trehalose, lactose, maltose, sucrose, cellobiose or raffinose residue.

Crosslinking via crosslinkers comprising a spacer group selected from the group consisting of di-, tri-, tetra-, and oligosaccharides provides a hydrogel product based entirely on carbohydrate type structures or derivatives thereof, which minimizes the disturbance of the crosslinking on the native properties of the glycosaminoglycans. The di-, tri-, tetra-, or oligosaccharide is preferably well defined in terms of structure and molecular weight. Preferably the spacer is selected from one specific di-, tri-, tetra-, or oligosaccharide structure. Preferably, the di-, tri-, tetra-, or oligosaccharide is mono-disperse or has a narrow molecular weight distribution. Using well defined di-, tri-, tetra-, or oligosaccharide based crosslinkers together with a highly efficient condensation reaction allows the product to be assembled in a controlled fashion. The crosslinker itself can also contribute to maintained or increased properties of the hydrogel, for example when crosslinking with a structure that correlates to hyaluronic acid (e.g. diamino hyaluronic acid tetrasaccharide) or when crosslinking with a structure with high water retention properties (e.g. trehalose).

The GAG may for example be sulfated or non-sulfated glycosaminoglycans such as hyaluronan, chondroitin sulphate, heparan sulphate, heparosan, heparin, dermatan sulphate and keratan sulphate. In some embodiments the GAG is hyaluronic acid, chondroitin or chondroitin sulfate. In a preferred embodiment the GAG is hyaluronic acid.

In preferred embodiments, the GAG is a native GAG. The GAG used in connection with the invention is preferably a naturally occurring GAG. The GAG is preferably used in its native state. I.e., the chemical structure of the GAG has preferably not been altered or modified by addition of functional groups or the like. Using the GAG in its native state is preferred because this will afford a crosslinked structure more closely resembling the natural molecules, which conserves the native properties and effects of the GAG itself, and can minimize the immune response when the crosslinked GAG is introduced into the body.

The covalently crosslinked GAG molecules preferably consist, or essentially consist of carbohydrate type structures or derivatives thereof. This means that the crosslinked GAG molecules are preferably free, or essentially free from synthetic non-carbohydrate structures or linkers. This can be achieved by using a GAG in its native state together with a crosslinker which consist, or essentially consist of carbohydrate type structures or derivatives thereof. Functional groups of the crosslinker are then covalently bound directly to carboxyl groups of the GAG. The crosslinks of the covalently crosslinked GAG thus preferably consist, or essentially consist of di-, tri-, tetra-, and oligosaccharide spacer groups.

The present invention provides according to a second aspect a process of preparing a hydrogel product comprising crosslinked glycosaminoglycan molecules, comprising the steps of:
(a) providing a solution of glycosaminoglycan molecules;
(b) activating carboxyl groups on the glycosaminoglycan molecules with a coupling agent to form activated, glycosaminoglycan molecules;
(c) crosslinking the activated glycosaminoglycan molecules via their activated carboxyl groups using a di- or multinucleophile functional crosslinker comprising a spacer group selected from the group consisting of di-, tri-, tetra-, and oligosaccharides to obtain crosslinked glycosaminoglycan molecules.

The present invention involves crosslinking of glycosaminoglycan molecules by covalent bonds, preferably amide bonds, typically using an activating agent for the carboxyl groups on the glycosaminoglycan molecule backbone and a di- or multinucleophile functional crosslinker comprising a spacer group selected from the group consisting of di-, tri-, tetra-, and oligosaccharides. Crosslinking according to the inventive method can be achieved by mild and efficient routes resulting in high yields with minimal degradation of the GAG molecules.

The di- or multinucleophile functional crosslinker contains a spacer group selected from the group consisting of di-, tri-, tetra-, and oligosaccharides, which remains in the crosslinks between the GAG molecules. The di- or multinucleophile functional di-, tri-, tetra-, and oligo-saccharides comprise at least two nucleophile functional groups attached thereto. The at least two nucleophile functional groups are preferably separated by the spacer group selected from the group consisting of di-, tri-, tetra-, and oligosaccharides.

The di- or multinucleophile functional crosslinker comprises two or more functional groups capable of reacting with functional carboxyl groups of the GAG, resulting in the formation of covalent bonds, preferably amide bonds. The nucleophile functional groups are preferably capable of reacting with carboxyl groups on the glycosaminoglycan molecule to form amide bonds. In some embodiments the nucleophile functional groups of the di-, tri-, tetra-, and oligosaccharides are selected from the group consisting of primary amine, hydrazine, hydrazide, carbazate, semi-carbazide, thiosemicarbazide, thiocarbazate and aminoxy.

The di- or multinucleophile functional di-, tri-, tetra-, and oligo-saccharides may be derived from nucleophile functional polysaccharides, such as chitobiose derived from chitin. The di- or multinucleophile functional di-, tri-, tetra-, and oligo-saccharides may also be di-, tri-, tetra-, and oligo-saccharides which have been modified by introduction of two or more nucleophile functional groups.

A preferred group of di- or multinucleophile functional crosslinker includes homo- or heterobifunctional primary amines, hydrazines, hydrazides, carbazates, semi-carbazides, thiosemicarbazides, thiocarbazates and aminoxy.

In certain embodiments, the activation step (b) and the crosslinking step (c) occur simultaneously. In other embodiments, the activation step (b) occurs prior to and separately from the crosslinking step (c).

In a preferred embodiment, step (c) further comprises providing particles of the crosslinked GAG molecule, having an average size in the range of 0.01-5 mm, preferably 0.1-0.8 mm.

In one preferred embodiment, the coupling agent of step (b) is a peptide coupling reagent. The peptide coupling reagent may be selected from the group consisting of triazine-based coupling reagents, carbodiimide coupling reagents, imidazolium-derived coupling reagents, Oxyma and COMU. A preferred peptide coupling reagent is a triazine-based coupling reagent, including the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT), preferably DMTMM. Another preferred peptide coupling reagent is a carbodiimide coupling reagent, preferably N-(3-dimethylaminopropyl)-N'-ethylcarbodiimide (EDC) combined with N-hydroxysuccinimide (NHS).

According to a related aspect, the present invention also provides use of the hydrogel product as a medicament, such as in the treatment of soft tissue disorders. There is provided a method of treating a patient suffering from a soft tissue disorder by administering to the patient a therapeutically effective amount of the hydrogel product. There is also provided a method of providing corrective or aesthetic treatment to a patient by administering to the patient a therapeutically effective amount of the hydrogel product.

Other aspects and preferred embodiments of the present invention will be evident from the following detailed disclosure of the invention and the appended claims.

ITEMIZED LISTING OF PREFERRED EMBODIMENTS

1. A hydrogel product comprising glycosaminoglycan molecules as the swellable polymer, wherein the glycosaminoglycan molecules are covalently crosslinked via crosslinks comprising a spacer group selected from the group consisting of di-, tri-, tetra-, and oligosaccharides.

2. A hydrogel product according to embodiment 1, wherein the glycosaminoglycan molecules are selected from the group consisting of hyaluronic acid, chondroitin and chondroitin sulfate, and mixtures thereof.

3. A hydrogel product according to embodiment 2, wherein the glycosaminoglycan molecules are hyaluronic acid.

4. A hydrogel product according to any one of the preceding embodiments, wherein at least 75% of the crosslinks comprise a spacer group selected from the group consisting of di-, tri-, tetra-, and oligosaccharides.

5. A hydrogel product according to embodiment 4, wherein at least 90% of the crosslinks comprise a spacer group selected from the group consisting of di-, tri-, tetra-, and oligosaccharides.

6. A hydrogel product according to embodiment 5, wherein at least 95% of the crosslinks comprise a spacer group selected from the group consisting of di-, tri-, tetra-, and oligosaccharides.

7. A hydrogel product according to any one of the preceding embodiments, wherein the spacer group is a hyaluronic acid tetrasaccharide, hyaluronic acid hexasaccharide, trehalose, lactose, maltose, sucrose, cellobiose or raffinose residue.

8. A hydrogel product according to embodiment 7, wherein the spacer group is a hyaluronic acid tetrasaccharide or hyaluronic acid hexasaccharide residue.

9. A hydrogel product according to embodiment 7, wherein the spacer group is a trehalose, lactose, maltose, sucrose, cellobiose or raffinose residue.

10. A hydrogel product according to any one of the preceding embodiments, wherein the spacer group is selected from the group consisting of di-, tri-, and tetrasaccharides.

11. A hydrogel product according to any one of the preceding embodiments, wherein the crosslinks are bound to the glycosaminoglycan molecules by amide bonds.

12. A hydrogel product according to any one of the preceding embodiments, wherein at least 75% of the bonds between glycosaminoglycan molecules and crosslinks are amide bonds.

13. A hydrogel product according to embodiment 12, wherein at least 90% of the bonds between glycosaminoglycan molecules and crosslinks are amide bonds.

14. A hydrogel product according to embodiment 13, wherein at least 95% of the bonds between glycosaminoglycan molecules and crosslinks are amide bonds.

15. A hydrogel product according to any one of the preceding embodiments, wherein less than 5% of the bonds between glycosaminoglycan molecules and crosslinks are ester bonds.

16. A hydrogel product according to embodiment 15, wherein less than 1% of the bonds between glycosaminoglycan molecules and crosslinks are ester bonds.

17. A hydrogel product according to any one of the preceding embodiments, wherein the crosslinked glycosaminoglycan molecule is in the form of gel particles having an average size in the range of 0.01-5 mm, preferably 0.1-0.8 mm.

18. A hydrogel product according to any one of the preceding embodiments, in the form of an injectable formulation.

19. A process of preparing a hydrogel product comprising crosslinked glycosaminoglycan molecules, comprising the steps of:
(a) providing a solution of glycosaminoglycan molecules;
(b) activating carboxyl groups on the glycosaminoglycan molecules with a coupling agent to form activated, glycosaminoglycan molecules;
(c) crosslinking the activated glycosaminoglycan molecules via their activated carboxyl groups using a di- or multi-nucleophile functional crosslinker comprising a spacer group selected from the group consisting of di-, tri-, tetra-, and oligosaccharides to obtain crosslinked glycosaminoglycan molecules.

20. A process according to embodiment 19, wherein the crosslinking of step (c) provides amide bonds between glycosaminoglycan molecules and crosslinkers.

21. A process according to any one of embodiments 19-20, wherein the activation step (b) and the crosslinking step (c) occur simultaneously.

22. A process according to any one of embodiments 19-21, wherein the coupling agent and the crosslinker are added to the glycosaminoglycan simultaneously.

23. A process according to any one of embodiments 19-20, wherein the activation step (b) occurs prior to and separately from the crosslinking step (c).

24. A process according to any one of embodiments 19-23, wherein step (c) further comprises providing particles of the crosslinked glycosaminoglycan, having an average size in the range of 0.01-5 mm, preferably 0.1-0.8 mm.

25. A process according to any one of embodiments 19-24, wherein the glycosaminoglycan molecules are selected from the group consisting of hyaluronic acid, chondroitin and chondroitin sulfate, and mixtures thereof.

26. A process according to any one of embodiments 19-25, wherein the glycosaminoglycan molecules are hyaluronic acid.

27. A process according to any one of embodiments 19-26, wherein the coupling agent of step (b) is a peptide coupling reagent.

28. A process according to embodiment 27, wherein the peptide coupling reagent is selected from the group consisting of triazine-based coupling reagents, carbodiimide coupling reagents, imidazolium-derived coupling reagents, Oxyma and COMU.

29. A process according to embodiment 28, wherein the peptide coupling reagent is a triazine-based coupling reagent.

30. A process according to embodiment 29, wherein the triazine-based coupling reagent is selected from the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT).

31. A process according to embodiment 30, wherein the triazine-based coupling reagent is DMTMM.

32. A process according to embodiment 28, wherein the peptide coupling reagent is a carbodiimide coupling reagent.

33. A process according to embodiment 32, wherein the carbodiimide coupling reagent is N-(3-dimethylaminopropyl)-N'-ethylcarbodiimide (EDC) combined with N-hydroxysuccinimide (NHS).

34. A process according to any one of embodiments 19-33, wherein the spacer group is a hyaluronic acid tetrasaccharide, hyaluronic acid hexasaccharide, trehalose, lactose, maltose, sucrose, cellobiose or raffinose residue.

35. A process according to any one of embodiments 19-33, wherein the spacer group is a hyaluronic acid tetrasaccharide or hyaluronic acid hexasaccharide residue.

36. A process according to any one of embodiments 19-33, wherein the spacer group is a trehalose, lactose, maltose, sucrose, cellobiose or raffinose residue.

37. A process according to any one of embodiments 19-36, wherein the spacer group is selected from the group consisting of di-, tri-, and tetrasaccharides.

38. A process according to any one of embodiments 19-37, wherein the nucleophilic groups of the crosslinker are selected from the group consisting of primary amine, hydrazine, hydrazide, carbazate, semi-carbazide, thiosemicarbazide, thiocarbazate and aminoxy.

39. A process according to embodiment 38, wherein the nucleophilic groups of the di-, tri-, tetra-, and oligosaccharides are primary amine.

40. A process according to embodiment 39, wherein the crosslinker is a dinucleofile functional crosslinker.

41. A process according to embodiment 40, wherein the crosslinker is selected from the group consisting of diamino hyaluronic acid tetrasaccharide, diamino hyaluronic acid hexasaccharide, diamino trehalose, diamino lactose, diamino maltose, diamino sucrose, chitobiose, or diamino raffinose.

42. A process according to any one of embodiments 19-41, further comprising the step:
(d) subjecting the crosslinked glycosaminoglycan molecules obtained in step (c) to alkaline treatment.

43. Product obtainable by the process according to any one of embodiments 19-42.

44. A hydrogel product according to any one of embodiments 1-18 and 43 for use as a medicament.

45. A hydrogel product according to embodiment 44 for use in the treatment of soft tissue disorders.

46. Use of a hydrogel product according to any one of embodiments 1-18 and 43 for the manufacture of a medicament for treatment of soft tissue disorders.

47. A method of treating a patient suffering from a soft tissue disorder by administering to the patient a therapeutically effective amount of a hydrogel product according to any one of embodiments 1-18 and 43.

48. A method of providing corrective or aesthetic treatment to a patient by administering to the patient a therapeutically effective amount of a hydrogel product according to any one of embodiments 1-18 and 43.

49. A method of cosmetically treating skin, which comprises administering to the skin a hydrogel product according to any one of embodiments 1-18 and 43.

DETAILED DESCRIPTION OF THE INVENTION

The present invention provides advantageous processes for preparing hydrogels made of crosslinked glycosaminoglycan (GAG) molecules, the resulting hydrogel products and uses thereof. GAGs are negatively charged heteropolysaccharide chains which have a capacity to absorb large amounts of water. In the hydrogel products according to the invention, the crosslinked GAG molecule is the swellable polymer which provides the gel properties. The preparation process described herein is mild to the GAG molecules but provides an efficient crosslinking.

Thus, the current invention provides GAG molecule hydrogels by crosslinking in aqueous media using di- or multinucleophile functional crosslinker capable of forming covalent bonds directly with carboxylic acid groups of GAG molecules by a reaction involving the use of a coupling agent.

The GAG according to the invention is preferably selected from the group consisting of hyaluronic acid, chondroitin and chondroitin sulfate. In a preferred embodiment, the GAG molecule is hyaluronic acid. Hyaluronic acid (HA) is one of the most widely used biocompatible polymers for medical and cosmetic use. HA is a naturally occurring polysaccharide belonging to the group of glycosaminoglycans (GAGs). Hyaluronic acid and products derived from hyaluronic acid are widely used in the biomedical and cosmetic fields, for instance during viscosurgery and as a dermal filler.

Unless otherwise provided, the term "hyaluronic acid" encompasses all variants and combinations of variants of hyaluronic acid, hyaluronate or hyaluronan, of various chain lengths and charge states, as well as with various chemical modifications. That is, the term also encompasses the various hyaluronate salts of hyaluronic acid with various counter ions, such as sodium hyaluronate. The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

The term "chondroitin" refers to GAGs having a disaccharide repeating unit consisting of alternating non-sulfated D-glucuronic acid and N-acetyl-D-galactosamine moieties. For avoidance of doubt, the term "chondroitin" does not encompass any form of chondroitin sulfate.

The term "chondroitin sulfate" refers to GAGs having a disaccharide repeating unit consisting of alternating D-glucuronic acid and N-acetyl-D-galactosamine moieties. The sulfate moiety can be present in various different positions. Preferred chondroitin sulfate molecules are chondroitin-4-sulfate and chondroitin-6-sulfate.

The chondroitin molecules can be obtained from various sources of animal and non-animal origin. Sources of non-animal origin include yeast and preferably bacteria. The molecular weight of a single chondroitin molecule is typically in the range of 1-500 kDa, but other molecular weights are possible.

The crosslinked GAG comprises crosslinks between the GAG molecule chains, which creates a continuous network of GAG molecules which is held together by the covalent crosslinks.

The GAG molecule chains are preferably crosslinked to each other via crosslinkers comprising a spacer group selected from the group consisting of di-, tri-, tetra-, and oligosaccharides.

It is preferred that the crosslinkers are bound to the glycosaminoglycan molecules by amide bonds.

The crosslinked GAG product is preferably biocompatible. This implies that no, or only very mild, immune response occurs in the treated individual. That is, no or only very mild undesirable local or systemic effects occur in the treated individual.

The crosslinked product according to the invention is a gel, or a hydrogel. That is, it can be regarded as a water-insoluble, but substantially dilute crosslinked system of GAG molecules when subjected to a liquid, typically an aqueous liquid.

The gel contains mostly liquid by weight and can e.g. contain 90-99.9%, water, but it behaves like a solid due to a three-dimensional crosslinked GAG molecule network within the liquid. Due to its significant liquid content, the gel is structurally flexible and similar to natural tissue, which makes it very useful as a scaffold in tissue engineering and for tissue augmentation. It is also useful for treatment of soft tissue disorder and for corrective or aesthetic treatment. It is preferably used as an injectable formulation.

Crosslinking of the GAG molecule may be achieved by activation with a coupling agent, followed by reaction with a crosslinking agent. The GAG molecule concentration and the extent of crosslinking affect the mechanical properties, e.g. the elastic modulus G', and stability properties, of the gel. Crosslinked GAG molecule gels can be characterized in terms of "degree of modification". The degree of modification of GAG molecule gels generally range between 0.01 and 15 mole %. The degree of modification (mole %) describes the amount of crosslinking agent(s) that is bound to the GAG molecule, i.e. molar amount of bound crosslinking agent(s) relative to the total molar amount of repeating disaccharide units. The degree of modification reflects to what degree the GAG molecule has been chemically modified by the crosslinking agent. Reaction conditions for activation and crosslinking and suitable analytical techniques for determining the degree of modification are all well known to the person skilled in the art, who easily can adjust these and other relevant factors and thereby provide suitable conditions to obtain a desirable degree of modification and verify the resulting product characteristics with respect to the degree of modification.

The hydrogel product may also comprise a portion of GAG molecules which are not crosslinked, i.e not bound to the three-dimensional crosslinked GAG molecule network. However, it is preferred that at least 50% by weight, preferably at least 60% by weight, more preferably at least 70% by weight, and most preferably at least 80% by weight, of the GAG molecules in a gel composition form part of the crosslinked GAG molecule network.

The crosslinked GAG molecule is preferably present in the form of gel particles. The gel particles preferably have an average size in the range of 0.01-5 mm, preferably 0.1-0.8 mm, such as 0.2-0.5 mm or 0.5-0.8 mm.

The hydrogel product may be present in an aqueous solution, but it may also be present in dried or precipitated form, e.g. in ethanol. The hydrogel product is preferably injectable.

The hydrogel product may be prepared by a process comprising the steps of:
(a) providing a solution of glycosaminoglycan molecules;
(b) activating carboxyl groups on the glycosaminoglycan molecules with a coupling agent to form activated, glycosaminoglycan molecules;
(c) crosslinking the activated glycosaminoglycan molecules via their activated carboxyl groups using a di- or multinucleophile functional crosslinker comprising a spacer group selected from the group consisting of di-, tri-, tetra-, and oligosaccharides to obtain crosslinked glycosaminoglycan molecules.

The GAG according to the invention is preferably selected from the group consisting of hyaluronic acid, chondroitin and chondroitin sulfate. In a preferred embodiment, the GAG molecule is hyaluronic acid.

In the activation step (b), the carboxyl groups on the GAG molecules are activated with a coupling agent to form activated GAG molecules.

In one preferred embodiment, the peptide coupling reagent is selected from the group consisting of triazine-based coupling reagents, carbodiimide coupling reagents, imidazolium-derived coupling reagents, Oxyma and COMU.

The peptide coupling reagent is preferably a triazine-based coupling reagent, such as 4-(4,6-dimethoxy-1,3,5-triazin-2-yl)-4-methylmorpholinium chloride (DMTMM) and 2-chloro-4,6-dimethoxy-1,3,5-triazine (CDMT). A preferred triazine-based peptide coupling reagent is DMTMM.

Other preferred peptide coupling reagent are carbodiimide coupling reagents, preferably N-(3-dimethylaminopropyl)-N'-ethylcarbodiimide (EDC) combined with N-hydroxysuccinimide (NHS).

In the crosslinking step (c), crosslinking of the activated GAG molecules occurs via their carboxyl groups using a crosslinker. The crosslinker is a di- or multinucleophile functional crosslinker comprising a spacer group selected from the group consisting of di-, tri-, tetra-, and oligosaccharides. The crosslinker connects the GAG chains to each other via carboxyl groups on the GAG backbone. The spacer group may for example be a hyaluronic acid tetrasaccharide, hyaluronic acid hexasaccharide, trehalose, lactose, maltose, sucrose, cellobiose or raffinose residue. By the term "residue" is meant here that the structure of the compound is similar but not identical to the patent compounds hyaluronic acid tetrasaccharide, hyaluronic acid hexasaccharide, trehalose, lactose, maltose, sucrose, cellobiose or raffinose respectively. The structure of the residue may differ from the structure of the parent compound in that it has been provided with two or more nucleofile functional groups and optionally covalently linked via said nucleofile functional groups carboxyl groups on the GAG backbone.

The di- or multinucleophile functional crosslinker comprises two or more functional groups capable of reacting with functional carboxyl groups of the GAG, resulting in the formation of covalent bonds, preferably amide bonds.

A preferred group of di- or multinucleophile functional crosslinker includes homo- or heterobifunctional primary amines, hydrazines, hydrazides, carbazates, semi-carbazides, thiosemicarbazides, thiocarbazates and aminoxy. Non limiting examples of such heterobifunctional crosslinkers useful in the present invention include:

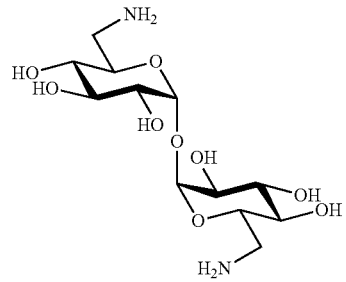

Diaminotrehalose (6,6'-diamino-6,6'-dideoxy trehalose);

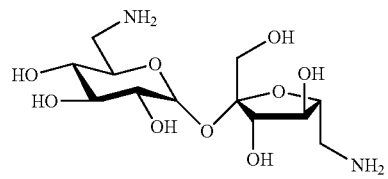

Diaminosucrose (6,6'-diamino-6,6'-dideoxy sucrose);

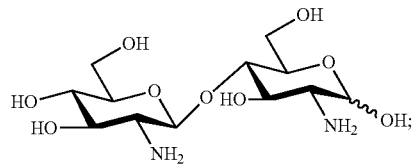

Chitobiose (2,2'-diamino-2,2'-dideoxy cellobiose)

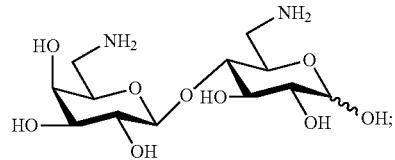

Diaminolactose (6,6'-diamino-6,6'-dideoxy lactose)

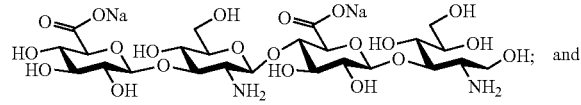

"Reduced N-Deacetylated hyaluronic acid tetrasaccharide" or "Reduced diamino hyaluronic acid tetrasaccharide"

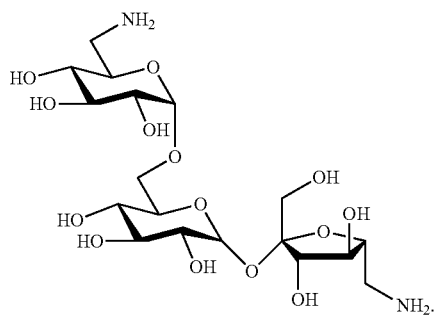

Diaminoraffinose (6,6''-diamino-6,6''-dideoxy raffinose)

Reaction schemes 1a-1h schematically illustrate examples of coupling by heterobifunctional primary amine (1a), aminoxy (1 b), carbazate (1c), semi-carbazide (1d), thiosemicarbazide (1e), thiocarbazate (1f), hydrazine (1g) and hydrazide (1h)
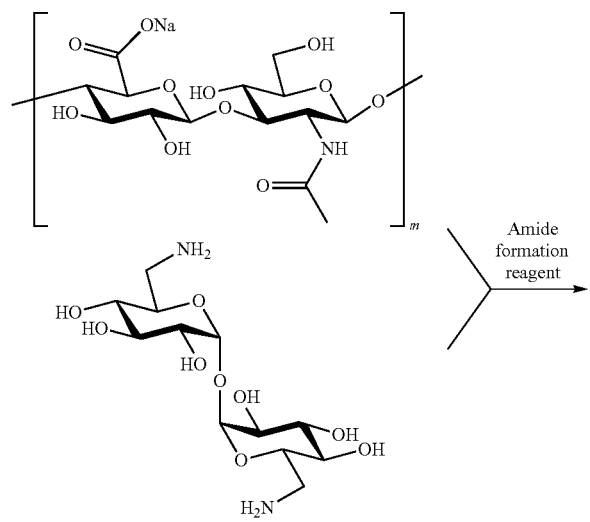
Scheme 1a
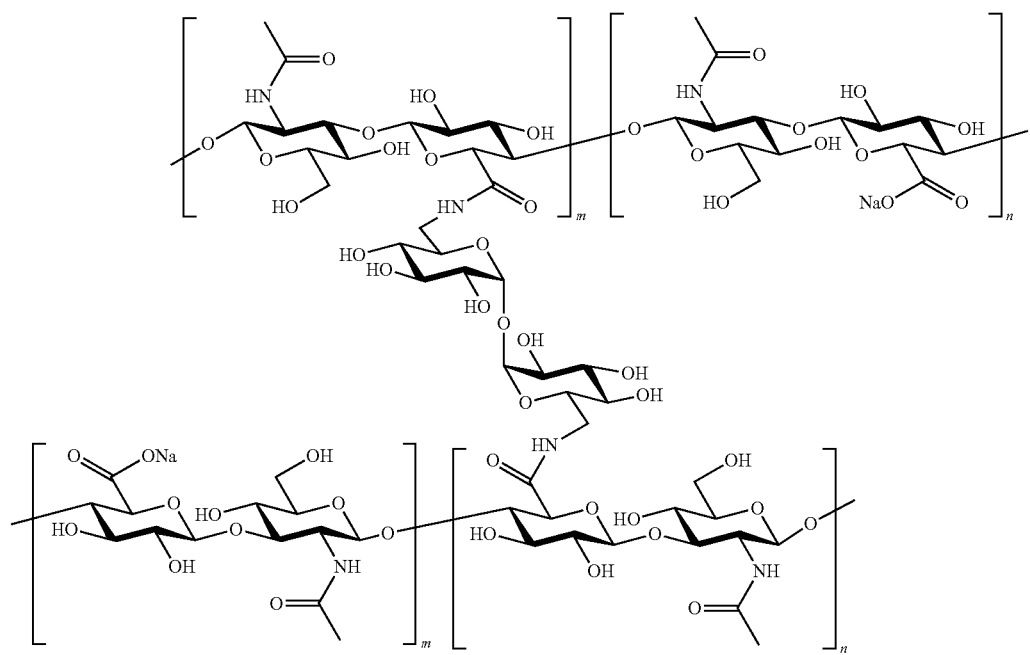

Scheme 1b
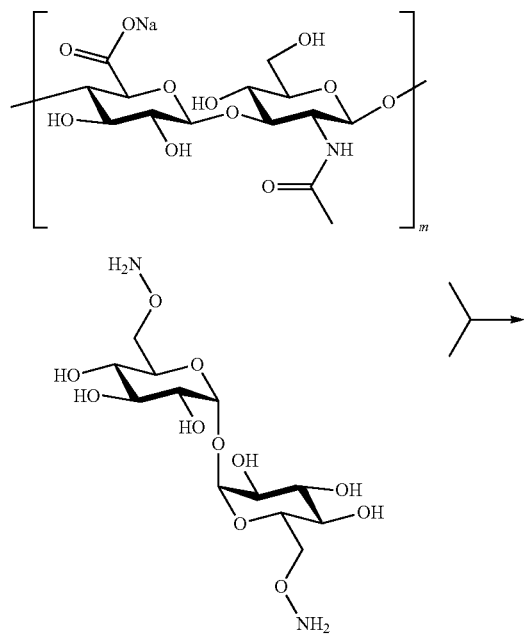
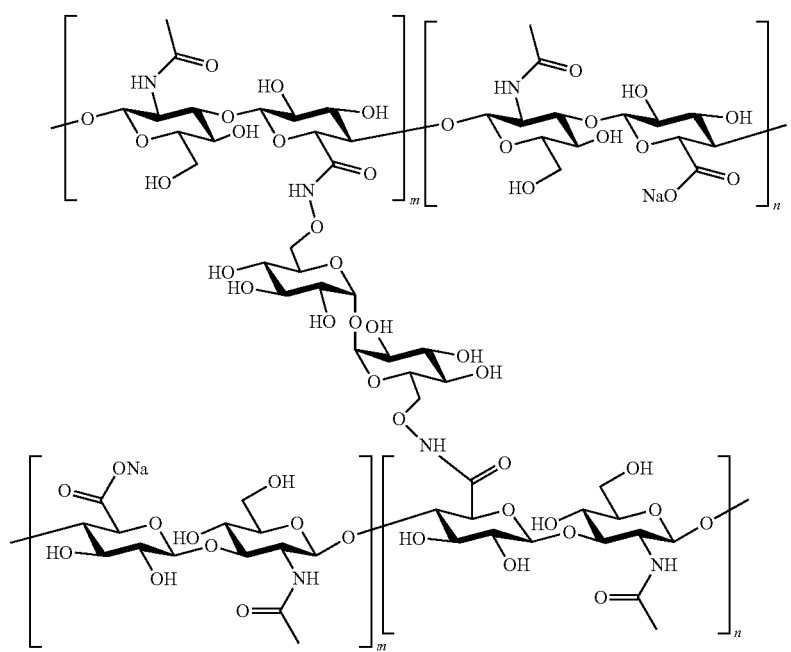

Scheme 1c
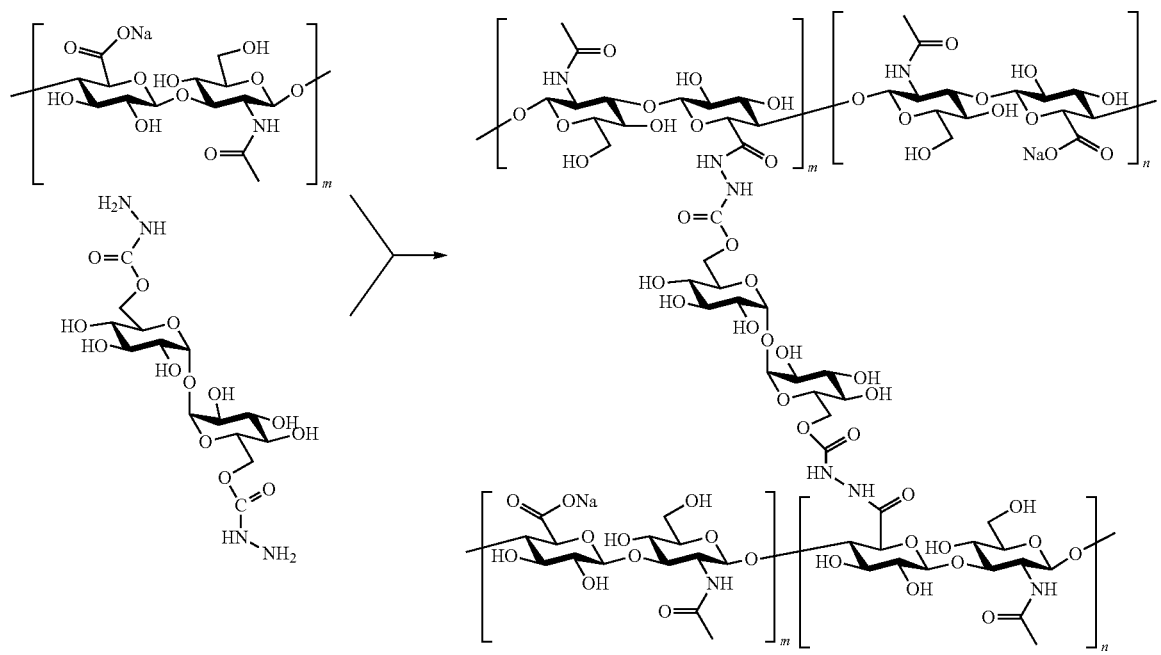
Scheme 1d
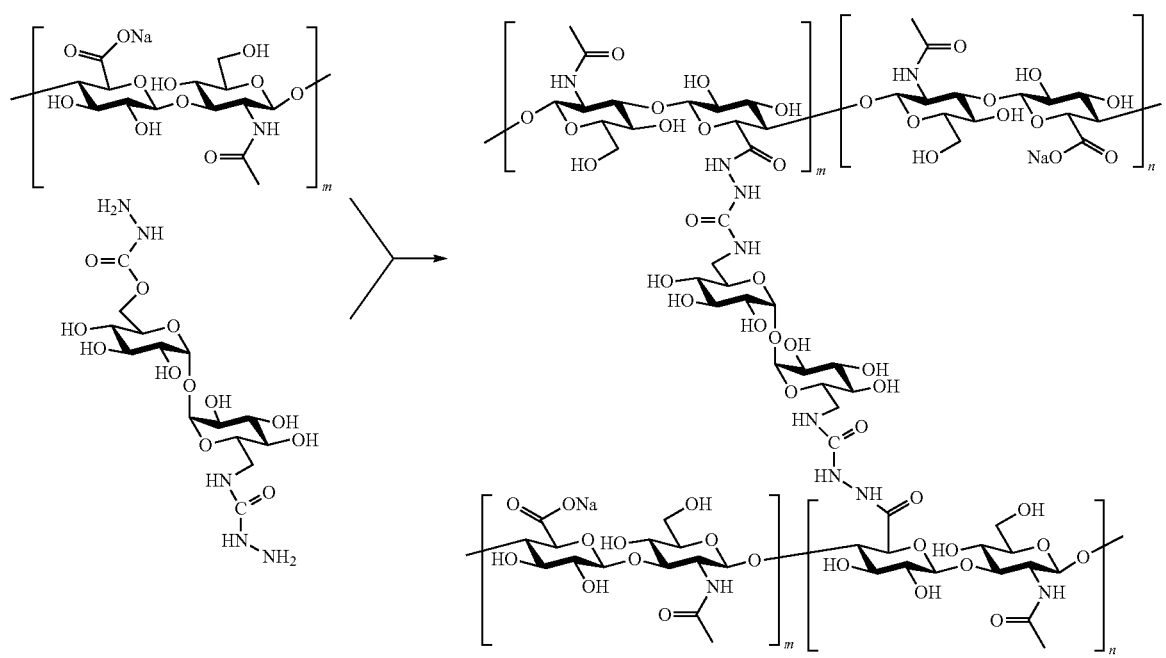

Scheme 1e
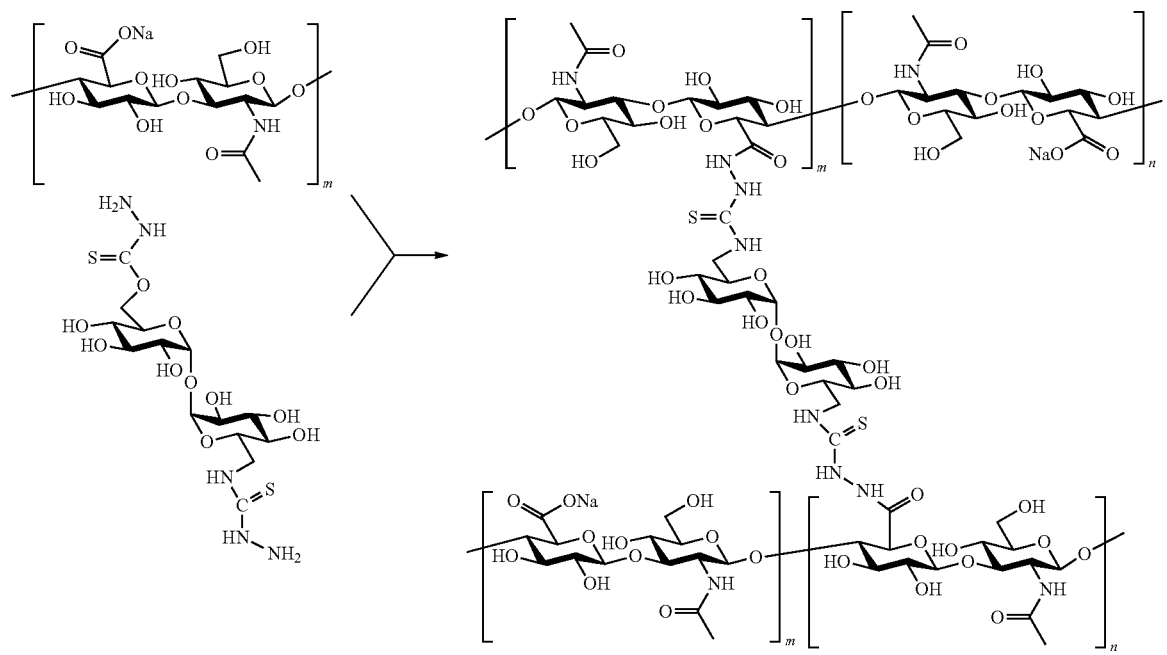
Scheme 1f
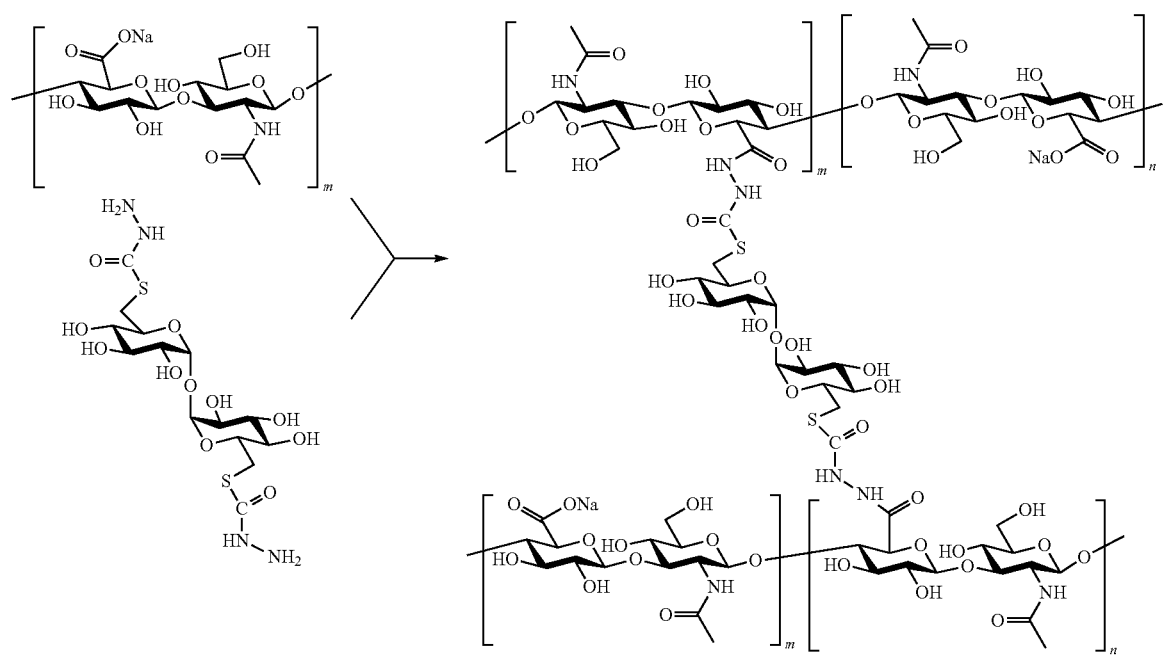

Scheme 1g
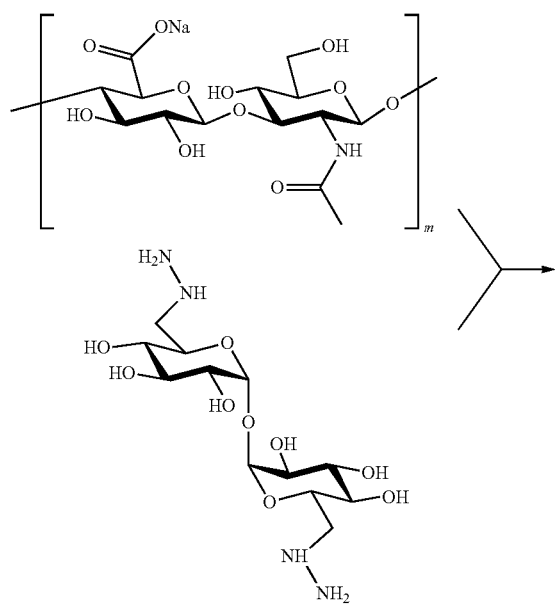
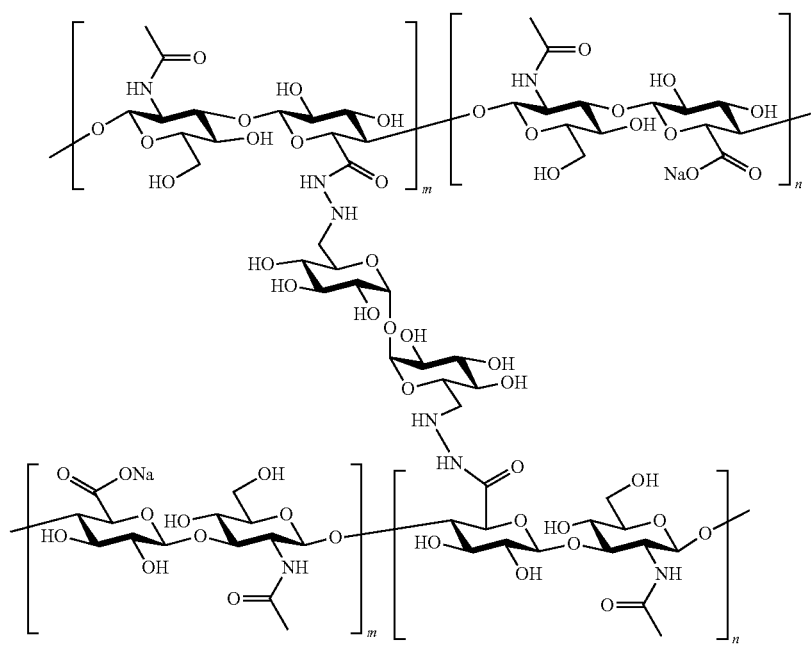

Scheme 1h

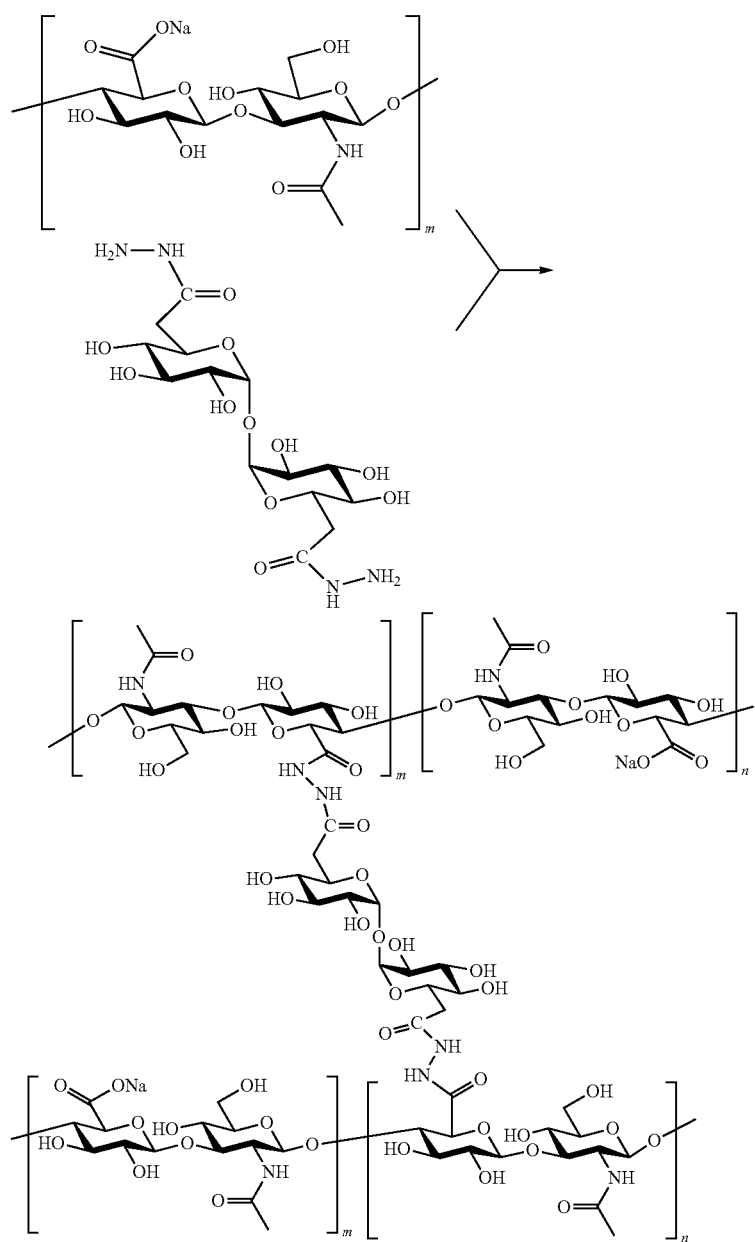

The di- or multinucleophile functional crosslinker contains a spacer group selected from the group consisting of di-, tri-, tetra-, and oligosaccharides, which remains in the crosslinks between the GAG molecules.

The process may be performed in a one-pot approach in aqueous media, involving the covalent coupling of di- or multinucleophile functional crosslinkers directly to inherent carboxylic acid groups on the native GAGs using a suitable coupling agent. In a preferred embodiment, the activation step (b) and the crosslinking step (c) occur simultaneously.

In another embodiment, the activation step (b) occurs prior to and separately from the crosslinking step (c).

The process for generating the crosslinked hydrogel typically involves preparing a mixture of a GAG molecule, such as hyaluronic acid together with a crosslinker agent, such as diamino trehalose, DATH, (0.001-10 molar equivalents of amine towards carboxylic acid groups, or preferably 0.001-1 molar equivalents) and a coupling agent such as DMTMM (0.01-10 molar equivalents to carboxylic acid groups, or preferably 0.05-1 molar equivalents). Incubating the mixture at 5-50° C., preferably 10-40° C. or even more preferred 20-35° C., during 2-120 hours, preferably 4-48 hours, followed by alkaline treatment, neutralization, precipitation, washing and dried under vacuum, yields a crosslinked polysaccharide as a solid. The precipitate was swelled in phosphate buffer containing NaCl to form a hydrogel, the hydrogel is preferably micronized to hydrogel particles in the size of 0.01-5 mm, preferably 0.1-1 mm.

A typical application of the resulting hydrogel product involves the preparation of injectable formulations for treatment of soft tissue disorders, including, but not limited to, corrective and aesthetic treatments.

In one more specific embodiment, crosslinking of chondroitin sulfate with DATH may be achieved as follows:

Diaminotrehalose (DATH) is synthesized as described in "*Synthetic Carbohydrate Polymers Containing Trehalose Residues in the Main Chain: Preparation and Characteristic Properties*"; Keisuke Kurita, * Naoko Masuda, Sadafumi Aibe, Kaori Murakami, Shigeru Ishii, and Shin-Ichiro Nishimurat; *Macromolecules* 1994, 27, 7544-7549.

Chondroitin Sulfate (CS) (10-200 kDa) is weighed in a Falcon tube. A stock solution of diaminotrehalose (DATH) is prepared by dissolving DATH in phosphate buffer pH 7.4. DMTMM is weighed in a vessel and the DATH-solution is added to the DMTMM. The pH of the DMTMM-DATH solution is adjusted to approx. 7 by addition of 1.2 M HCl or 0.25 M NaOH, and the mixture is subsequently added to CS. The contents are thoroughly homogenized and then incubated at 15-55° C. for 2-48 h. The resulting material is pressed through a 1 mm steel mesh two times and swelled in NaOH. The gel is neutralized with 1.2 M HCl to pH 7 and precipitated with ethanol. The resulting precipitate is washed with 100 mM NaCl in 70% ethanol, with 70% ethanol and ethanol. The obtained solid is dried at 25° C. under vacuum. The precipitate is swelled in 0.7% NaCl phosphate buffer pH 7.4 and pressed through a filter mesh three times. The crosslinked CS-gel is filled on syringes and sterilized.

In another more specific embodiment, crosslinking of HA with diaminosucrose may be achieved as follows:

Diaminosucrose is prepared as described in "*Library of mild and economic protocols for the selective derivatization of sucrose under microwave irradiation*"; M. Teresa Barros, Krasimira T. Petrova, Paula Correia-da-Silva and Taterao M. Potewar; *Green Chem.,* 2011, 13, 1897-1906.

Hyaluronic acid (HA) (10-1 000 kDa) is weighed in a vessel. A stock solution of diaminosucrose is prepared by dissolving diaminosucrose in phosphate buffer pH 7.4. DMTMM is weighed in a vessel and the diaminosucrose-solution is added to the DMTMM. The pH of the DMTMM-diaminosucrose solution is adjusted to approx. 7 by addition of 1.2 M HCl or 0.25 M NaOH, and the mixture is subsequent added to HA. The contents are thoroughly homogenized and then incubated at 15-55° C. for 2-48 h. The resulting material is pressed through a 1 mm steel mesh two times and swelled in NaOH. The gel is neutralized with 1.2 M HCl to pH 7 and precipitated with ethanol. The resulting precipitate is washed with 100 mM NaCl in 70% ethanol, with 70% ethanol and ethanol. The obtained solid is dried at 25° C. under vacuum. The precipitate is swelled in 0.7% NaCl phosphate buffer pH 7.4 and pressed through a filter mesh three times. The crosslinked HA-gel is filled on syringes and sterilized.

In another more specific embodiment, crosslinking of HA with chitobiose may be achieved as follows:

Hyaluronic acid (HA) (10-1 000 kDa) is weighed in a vessel. A stock solution of chitiobiose (purchased from Carbosynth Ltd. UK) is prepared by dissolving chitobiose in phosphate buffer pH 7.4. DMTMM is weighed in a vessel and the chitobiose-solution is added to the DMTMM. The pH of the DMTMM-chitobiose solution is adjusted to approx. 7 by addition of 1.2 M HCl or 0.25 M NaOH, and the mixture is subsequent added to HA. The contents are thoroughly homogenized and then incubated at 15-55° C. for 2-48 h. The resulting material is pressed through a 1 mm steel mesh two times and swelled in NaOH. The gel is neutralized with 1.2 M HCl to pH 7 and then precipitated with ethanol. The resulting precipitate is washed with 100 mM NaCl in 70% ethanol, with 70% ethanol and ethanol. The obtained solid is dried at 25° C. under vacuum. The precipitate is swelled in 0.7% NaCl phosphate buffer pH 7.4 and pressed through a filter mesh three times. The crosslinked HA-gel is filled on syringes and sterilized.

In another more specific embodiment, crosslinking of HA with a reduced diamino HA-tetrasaccharide may be achieved as follows:

Hyaluronic acid (HA) (10-1 000 kDa) is weighed in a vessel. A stock solution of a reduced diamino HA-tetrasaccharide is prepared by dissolving reduced diamino HA-tetrasaccharide in phosphate buffer pH 7.4. DMTMM is weighed in a vessel and the reduced diamino HA-tetrasaccharide solution is added to the DMTMM. The pH of the DMTMM and reduced diamino HA-tetrasaccharide solution is adjusted to approx. 7 by addition of 1.2 M HCl or 0.25 M NaOH, and the mixture is subsequent added to HA. The contents are thoroughly homogenized and incubated at 15-55° C. for 2-48 h. The resulting material is pressed through a 1 mm steel mesh two times and swelled in NaOH. The gel is neutralized with 1.2 M HCl to pH 7 and precipitated with ethanol. The resulting precipitate is washed with 100 mM NaCl in 70% ethanol, with 70% ethanol and ethanol. The obtained solid is dried at 25° C. under vacuum. The precipitate is swelled in 0.7% NaCl phosphate buffer pH 7.4 and pressed through a filter mesh three times. The crosslinked HA-gel is filled on syringes and sterilized.

In another more specific embodiment, crosslinking of HA with dicarbazate trehalose may be achieved as follows:

$\alpha,\alpha$-D-Trehalose (1 equiv.) (anhydrous) (Carbosynth Ltd. UK) is dissolved in dry dimethylformamid (DMF), and triethylamine (2-6 equiv.) is added subsequently. The flask is cooled to 0° C. (ice/water) and under $N_2$-atmosphere. 4-Nitrophenyl chloroformate (2-6 equiv.) is added into the flask dropwise. The resulting mixture is allowed to stir at room temperature for 2-48 h and then concentrated, purified by FC and dried under vacuum. The product is dissolved in DMF, and hydrazine monohydrate (2-20 equiv.) is added to the solution and stirred at 0-50° C. for 4-48 h. The reaction is then concentrated, purified by FC and dried under vacuum to obtain $\alpha,\alpha$-D-6,6'-dideoxy-6,6'-dicarbazate trehalose (dicarbazate trehalose, DCT).

Hyaluronic acid (HA) (10-1 000 kDa) is weighed in a vessel. A stock solution of dicarbazate trehalose (DCT) is prepared by dissolving DCT in phosphate buffer pH 7.4. DMTMM is weighed in a vessel and the DCT-solution is added to the DMTMM. The pH of the DMTMM-DCT solution is adjusted to approx. 7 by addition of 1.2 M HCl or 0.25 M NaOH, and the mixture is subsequent added to HA. The contents are thoroughly homogenized and incubated at 15-55° C. for 2-48 h. The resulting material is pressed through a 1 mm steel mesh two times and swelled in NaOH. The gel is neutralized with 1.2 M HCl to pH 7 and precipitated with ethanol. The resulting precipitate is washed with 100 mM NaCl in 70% ethanol, with 70% ethanol and ethanol. The obtained solid is dried at 25° C. under vacuum. The precipitate is swelled in 0.7% NaCl phosphate buffer pH 7.4 and then pressed through a filter mesh three times. The crosslinked HA-gel is filled on syringes and sterilized.

In another more specific embodiment, crosslinking of HA with diaminoxytrehalose may be achieved as follows:

To a stirred suspension of $\alpha,\alpha$-D-Trehalose (1 equiv.) (anhydrous) (Carbosynth Ltd. UK) in anhydrous THF, N-hydroxyphthalimide (2-10 equiv.) and triphenylphosphine (2-10 equiv.) is added, and the mixture is stirred for 5-60 min. Diisopropyl azodicarboxylate (DIAD, 2-10 equiv.) is then added dropwise at 0-40° C. and the mixture is stirred for 2-48 h at 0-40° C. The solvent is removed in vacuo and the crude product is purified by FC and dried under vacuum. A suspension of the product in a mixture of MeOH and $CH_2Cl_2$ is treated with hydrazine monohydrate (2-20 equiv.), and the mixture is stirred at 0-40° C. for 2-24 h followed by concentration, purification by FC and drying under vacuum to obtain the diaminoxytrehalose.

Hyaluronic acid (HA) (10-1 000 kDa) is weighed in a vessel. A stock solution of diaminoxytrehalose (DAOT) is prepared by dissolving DAOT in phosphate buffer pH 7.4. DMTMM is weighed in a vessel and the DAOT-solution is added to the DMTMM. The pH of the DMTMM-DAOT solution is adjusted to approx. 7 by addition of 1.2 M HCl or 0.25 M NaOH, and the mixture is subsequent added to HA. The contents are thoroughly homogenized and incubated at 15-55° C. for 2-48 h. The resulting material is pressed through a 1 mm steel mesh two times and swelled in NaOH. The gel is neutralized with 1.2 M HCl to pH 7 and precipitated with ethanol. The resulting precipitate is washed with 100 mM NaCl in 70% ethanol, with 70% ethanol and ethanol. The obtained solid is dried at 25° C. under vacuum. The precipitate is swelled in 0.7% NaCl phosphate buffer pH 7.4 and then pressed through a filter mesh three times. The crosslinked HA-gel is filled on syringes and sterilized.

EXAMPLES

Without desiring to be limited thereto, the present invention will in the following be illustrated by way of examples.

Definitions and Analysis

SwF—Swelling factor analysis was done in saline.
[PS]—Polysaccharide concentration, e.g. HA concentration. The PS concentration was measured with LC-SEC-UV or NIR.
GelP—Gel part (also sometimes referred to as gel content or GelC) is a description of the percentage of polysaccharide that is a part of the gel network. A number of 90% means that only 10% of polysaccharide is not a part of the network. The amount of free polysaccharide in the gel was measured with LC-SEC-UV.
SwC—swelling capacity is the total liquid uptake of one gram polysaccharide, not corrected for gel part.

$$SwC = \frac{SwF}{[PS]}$$

SwCC—Corrected swelling capacity (also sometimes referred to as SwDC) is the total liquid uptake of one gram polysaccharide, corrected for gel part.

$$SwCC = \frac{SwF}{GelP*[PS]}$$

CrR—Effective crosslinking ratio was analyzed with LC-SEC-MS and defined as:

$$CrR = \frac{\text{mol crosslinked crosslinker with amide bonds}}{\text{mol linked crosslinker with amide bonds}}$$

A CrR of 1.0 means that all of the crosslinker has crosslinked.

Alkaline or Heat Hydrolysis
In some of the examples below, the product was subjected to alkaline or heat hydrolysis in order to hydrolyze ester bonds formed during the crosslinking process. The alkaline/heat hydrolysis results in only amide crosslink bonds in the end product. The alkaline/heat hydrolysis was performed as follows:
Alkaline Hydrolysis
The material was swelled in 0.25 M NaOH (1 g material:9 g 0.25 M NaOH resulting in pH 13) for at least 1 h at room temperature. The gel was neutralized with 1.2 M HCl to pH 7 and then precipitated with ethanol. The resulting precipitate was washed with 100 mM NaCl in 70% ethanol to remove excess reagents and then with 70% ethanol to remove salts and finally with ethanol to remove water. Ethanol was removed in a vacuum dryer overnight.

The precipitate was swelled in 0.7% NaCl phosphate buffer pH 7.4 and then pressed through a fine filter mesh three times. The gel was filled on syringes and sterilized. In some cases a couple of the syringes were not sterilized to see the effect of sterilization.
Heat Hydrolysis
The material was swelled in 0.7% NaCl phosphate buffer pH 7.4 at room temperature. The pH was adjusted to 7.2-7.5 if needed. The gel was left at 70° C. for 20-24 h and then particle-size reduced through a fine filter mesh three times. The gel was filled on syringes and sterilized. In some cases a couple of the syringes were not sterilized to see the effect of sterilization.
Synthesis of Hyaluronic Diaminotrehalose
Diaminotrehalose (DATH) was synthesized as described in "*Synthetic Carbohydrate Polymers Containing Trehalose Residues in the Main Chain: Preparation and Characteristic Properties*"; Keisuke Kurita, * Naoko Masuda, Sadafumi Aibe, Kaori Murakami, Shigeru Ishii, and Shin-Ichiro Nishimurat; *Macromolecules* 1994, 27, 7544-7549.

Example 1—Crosslinking of Hyaluronic Acid with Diaminotrehalose (DATH)

A series of experiments (Examples 1-1 to 1-5) were performed which involved crosslinking of hyaluronic acid (HA) of different molecular weights with various molar ratios of DATH using 4-(4,6-dimethoxy-1,3,5-triazin-2-yl)-4-methylmorpholinium chloride (DMTMM) as a coupling agent. Ratios between HA, DATH and DMTMM are set out in Table 1 below.

The hyaluronan (molecular weight ($M_w$) from about 100 kDa to about 1 000 kDa) was weighed in a Falcon tube. A stock solution of diaminotrehalose (DATH) was prepared by dissolving DATH (0.001-0.005 equiv.) in phosphate buffer pH 7.4. DMTMM (0.05 equiv.) was weighed in a PTFE-container and the DATH-solution was added to DMTMM to dissolve it. The pH of the DMTMM-DATH solution was adjusted to 6-7 with 1.2 M HCl or 0.25 M NaOH and then added to the HA. The contents were thoroughly homogenized and then incubated at 35° C. for 24 h.

The resulting material was pressed through a 1 mm steel mesh two times and then treated with a NaOH solution. The gel was neutralized with 1.2 M HCl to pH 7 and then precipitated with ethanol. The resulting precipitate was washed with 100 mM NaCl in 70% ethanol to remove excess reagents and then with 70% ethanol to remove salts and finally with ethanol to remove water. Ethanol was removed in a vacuum dryer over night.

The precipitate was swelled in 0.7% NaCl phosphate buffer pH 7.4 and then pressed through a filter mesh three times. The gel was filled on syringes and sterilized.

TABLE 1

| Example | <$M_w$> (MDa) | Eq DMTMM | Eq DATH | Monophasic at [HA] 50 mg/mL | CrR | GelC (%) | SwCC (ml/g) |
|---|---|---|---|---|---|---|---|
| 1-1 | 1.06 | 0.05 | 0.003 | No | 0.99 | NA | NA |
| 1-2 | 1.06 | 0.05 | 0.001 | Yes | 0.99 | 74 | 101 |
| 1-3 | 0.64 | 0.05 | 0.005 | Yes | NA | 93 | 38 |
| 1-4 | 0.31 | 0.05 | 0.005 | Yes | NA | 85 | 49 |
| 1-5 | 0.11 | 0.05 | 0.005 | Yes | NA | 84 | 123 |

NA—not available since the analysis was not done

Example 2—Crosslinking of Hyaluronic Acid with Diaminotrehalose (DATH)

A series of experiments (Examples 2-1 to 2-11) were performed which involved crosslinking of hyaluronic acid (HA) of different molecular weights with various molar ratios of DATH using 4-(4,6-dimethoxy-1,3,5-triazin-2-yl)-4-methylmorpholinium chloride (DMTMM) as a coupling agent. Ratios between HA, DATH and DMTMM are set out in Table 2 below.

Hyaluronic acid was weighed in a reaction vessel. A stock solution of the crosslinker (DATH) was prepared by dissolving it in phosphate buffer pH 7.4. DMTMM was weighed in a PTFE-container and the crosslinker-solution was added to the DMTMM to dissolve it. The pH of the DMTMM-crosslinker solution was adjusted to 6-7 with 1.2 M HCl or 0.25 M NaOH and then added to the HA. The contents were thoroughly homogenized and then incubated at 35° C. for 24 h. The resulting material was pressed through a 1 mm steel mesh two times and then treated with either heat or alkaline. The results are displayed in Table 2.

TABLE 2

Summary crosslinking Hyaluronic Acid with (DATH)

| Example | <Mw> (MDa) | DMTMM/HA (mol %) | DATH/HA (mol %) | DMTMM/ DATH | Hydrolysis | CrR | GelP after sterilization (%) | SwCC (ml/g) |
|---|---|---|---|---|---|---|---|---|
| 2-1 | 1 | 5.0 | 0.08 | 61 | Alkaline | 0.99 | 74 | 101 |
| 2-2 | 1 | 0.7 | 0.06 | 12 | Heat | 0.51 | 45 | 309 |
| 2-3 | 1 | 2.4 | 0.03 | 74 | Heat | 0.94 | 55 | 259 |
| 2-4 (n = 4) | 0.6 | 1.2 | 0.32 | 3.6 | Heat | 0.45 | 72 ± 4 | 132 ± 23 |
| 2-5 (n = 4) | 0.6 | 1.2 | 0.32 | 3.6 | Alkaline | 0.43 | 63 ± 1 | 218 + 13 |
| 2-6 | 0.3 | 5.0 | 0.25 | 20 | Alkaline | | 77 | 79 |
| 2-7 | 0.2 | 4.9 | 0.57 | 8.7 | Heat | 0.86 | 77 | 106 |
| 2-8 | 0.2 | 4.0 | 0.57 | 7.0 | Alkaline | 0.63 | 52 | 445 |
| 2-9 | 0.1 | 4.5 | 0.65 | 7.0 | Heat | 0.55 | 50 | 337 |
| 2-10 | 0.1 | 6.9 | 0.79 | 8.8 | Heat | 0.89 | 91 | 91 |
| 2-11 | 0.1 | 5.5 | 0.65 | 8.5 | Heat | 0.75 | 87 | 146 |

Empty cells - no analysis done.

Example 3—Crosslinking of Hyaluronic Acid with Chitobiose (CB)

Hyaluronic acid was weighed in a reaction vessel. A stock solution of the crosslinker (chitobiose) was prepared by dissolving it in phosphate buffer pH 7.4. DMTMM was weighed in a PTFE-container and the crosslinker-solution was added to the DMTMM to dissolve it. The pH of the DMTMM-crosslinker solution was adjusted to 6-7 with 1.2 M HCl and then added to the HA. The contents were thoroughly homogenized and then incubated at 35° C. for 24 h. The resulting material was pressed through a 1 mm steel mesh two times and then treated with either heat or alkaline according to the general procedures. Ratios between HA, chitobiose and DMTMM are set out below in Table 3 (Examples 3-1 to 3-2).

Example 4—Crosslinking of Hyaluronic Acid with Diaminotetra-HA (DA-4HA)

Diaminotetra-HA (DA-4HA) was synthesized according to below scheme:

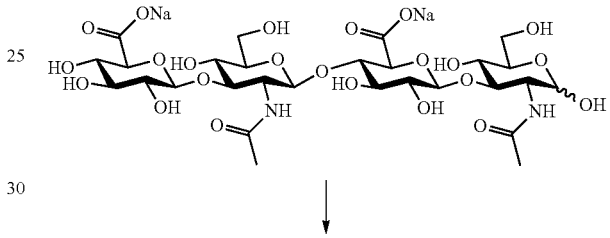

-continued

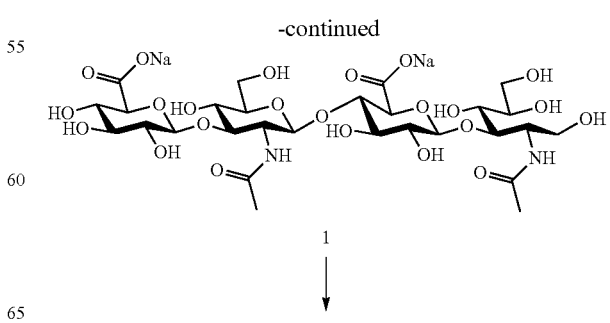

-continued

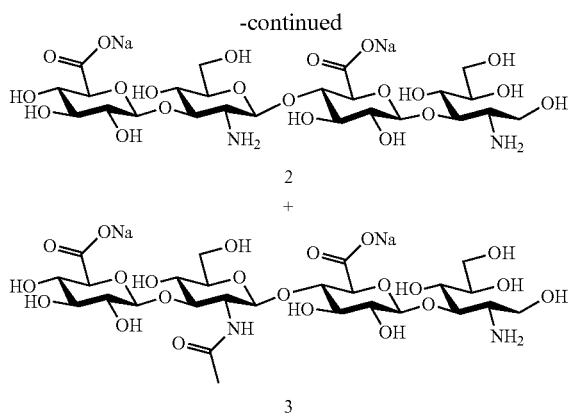

Step 1

A solution of HA-4 (500 mg, 0.61 mmol) in water (5 ml) at room temperature was treated with sodium borohyride (23.05 mg, 0.61 mmol) and the resulting solution was stirred for 3 h, concentrated to dryness to afford the reduced product 1 (532 mg, assumed 100%) as a white foam.

LCMS ($t_r$=0.28 min., ES+=779.4 (M-2 Na+2H)

Step 2

The reduced product 1 (532 mg) was dissolved in aqueous $NH_2OH$ (5 ml, 50% v/v/) and solid $NH_4I$ (100 mg) was added. The resulting suspension was heated at 70° C. for 48 h, cooled to room temperature and concentrated to dryness to afford a residue. The residue was precipitated in neat EtOH and the resulting precipitate was collected by filtration and dried to a constant weight to afford the a 1:1 mixture of diamine 2 and mono-amine 3 in quantitative yield. The crude reaction product was used without further purification.

2: LCMS ($t_r$=0.16 min., ES+=695.36 (M-2 Na+2H)

3: LCMS ($t_r$=0.19 min., ES+=737.47 (M-2 Na+2H)

Hyaluronic acid was weighed in a reaction vessel. A stock solution of the crosslinker (diaminotetra-HA), synthesized as described above, and DMTMM respectively were prepared by dissolving it in phosphate buffer pH 7.4. The pH of the solutions were adjusted to 7 and then added to the HA. The contents were thoroughly homogenized and then incubated at 23° C. for 24 h. The resulting material was pressed through a 1 mm steel mesh two times and then treated with heat according to the general procedures. Ratio between HA, diaminotetra-HA and DMTMM are set out below in Table 3 (Example 4).

Example 5—Crosslinking of Heparosan (HEP) with Diaminotrehalose (DATH)

The coupling agent DMTMM and the crosslinker DATH were weighed in separate reaction vessels and dissolved in phosphate buffer (pH 7.4). The solutions pH was adjusted to pH 7-7.5 with 1.2 M HCl or 0.25 M NaOH. Thereafter, DMTMM- and DATH-solutions were successively added to the heparosan weighed in a reaction vessel. The contents were thoroughly homogenized and then incubated at 35° C. for 24 h. The resulting material was pressed through a 1 mm steel mesh two times and then treated with heat according to the general procedures. Ratios between heparosan, DATH and DMTMM are set out in Table 3 below (Examples 5-1 to 5-2).

Example 6—Crosslinking of Chondroitin Sulfate (CS) with Diaminotrehalose (DATH)

The coupling agent DMTMM and the crosslinker DATH were weighed in separate reaction vessels and dissolved in phosphate buffer (pH 7.4). The solutions pH was adjusted to pH 7-7.5 with 1.2 M HCl or 0.25 M NaOH. Thereafter, DMTMM- and DATH-solutions were successively added to the chondroitin sulfate weighed in a reaction vessel. The contents were thoroughly homogenized and then incubated at 35° C. for 24 h. The resulting material was pressed through a 1 mm steel mesh two times and then treated with heat according to the general procedures. Ratios between chondroitin sulfate, DATH and DMTMM are set out below in Table 3 (Examples 6-1 to 6-2).

TABLE 3

Summary crosslinking examples 3-6

| Example | PS Mw | Crosslinker | DMTMM/PS (mol %) | Crosslinker/PS (mol %) | DMTMM/crosslinker | Hydrolysis | GelP (%) | SwCC (mL/g) | SwC (mL/g) | G' 0.1 Hz (kPa) |
|---|---|---|---|---|---|---|---|---|---|---|
| 3-1 | HA 1 MDa | CB | 2.4 | 0.13 | 18.5 | Heat | 60 | 224 | | |
| 3-2 | HA 1 MDa | CB | 2.4 | 0.13 | 18.5 | Alkaline | 45 | 335 | | |
| 4 | HA 0.2 MDa | DA-4HA | 24 | 1.0 | 24 | Heat | | | 47 | |
| 5-1 | HEP 140 kDa | DATH | 7 | 1.0 | 7 | Heat | 36 | 175 | | |
| 5-2 | HEP 140 kDa | DATH | 10.5 | 1.5 | 7 | Heat | 80 | 101 | | |
| 6-1 | CS 30 kDA | DATH | 35 | 5.0 | 7.0 | Heat | | | 48 | 1.6 |
| 6-2 | CS 30 kDa | DATH | 35 | 5.0 | 7.0 | Heat | | | 44 | 1.5 |

PS = polysaccharide,
HA = hyaluronan,
HEP = heparosan,
CS = chondroitin sulfate,
DA-4HA = diaminotetra-HA,
CB = chitobiose
Empty cells - no analysis done.

The invention claimed is:

1. A process of preparing a hydrogel product comprising crosslinked hyaluronic acid (HA) molecules, the process comprising:
    (a) activating carboxyl groups on the HA molecules with a coupling agent to form activated HA molecules;
    (b) crosslinking the activated HA molecules via their activated carboxyl groups using diaminotrehalose to obtain crosslinked HA molecules; and
    (c) hydrolyzing ester bonds in the crosslinked HA molecules via alkaline hydrolysis to obtain a hydrogel product having less than 50% non-crosslinked HA molecules by weight of the hydrogel product, and
    wherein the crosslinked HA molecules are free from synthetic non-carbohydrate structures and synthetic non-carbohydrate linkers.

2. The process according to claim 1, wherein the crosslinking provides amide bonds between HA molecules and crosslinkers.

3. The process according to claim 1, wherein the coupling agent is a triazine-based coupling reagent.

4. The process according to claim 1, wherein hydrolyzing the ester bonds comprises swelling the crosslinked HA molecules in an alkaline solution for at least 1 hour.

5. The process according to claim 4, further comprising:
    (d) neutralizing the crosslinked HA molecules to a neutral pH;
    (e) precipitating the neutralized crosslinked HA molecules;
    (f) drying the precipitated crosslinked HA molecules; and
    (g) swelling the dried crosslinked HA molecules in a phosphate buffer.

6. The process according to claim 1, wherein (a) and (b) occur simultaneously.

7. The process according to claim 4, wherein the alkaline solution comprises a hydroxide.

8. The process according to claim 1, wherein less than 20% by weight of the hydrogel product obtained in (c) comprises HA molecules that are not crosslinked.

9. The process according to claim 1, wherein the crosslinked HA molecules are in the form of gel particles.

10. The process according to claim 9, wherein the gel particles are 0.01 mm to 1 mm in size.

11. The process according to claim 1, wherein the HA molecules, prior to crosslinking, have a molecular weight of about 1,000 kDa.

* * * * *